United States Patent [19]
Goldberg

[11] Patent Number: 6,013,089
[45] Date of Patent: Jan. 11, 2000

[54] TONGUE CLEANER

[76] Inventor: Barry A. Goldberg, 13882 N. Kendall Dr., Miami, Fla. 33186

[21] Appl. No.: 09/061,643

[22] Filed: Apr. 17, 1998

[51] Int. Cl.$^7$ .................................................. A61B 17/00
[52] U.S. Cl. ........................................................ 606/161
[58] Field of Search ..................... 606/161, 160, 606/1; 15/111, 110, 167.1, 160; 132/309; D24/147, 176, 152

[56] References Cited

U.S. PATENT DOCUMENTS

| | | | |
|---|---|---|---|
| 1,893,524 | 1/1933 | Shanley | 606/161 |
| 2,049,956 | 8/1936 | Greenber | 606/161 |
| 3,683,924 | 8/1972 | Louie | 606/161 |
| 4,582,059 | 4/1986 | Tiwari | 606/161 |
| 5,569,278 | 10/1996 | Persad | 606/161 |

*Primary Examiner*—Michael Buiz
*Assistant Examiner*—Vikki Trinh
*Attorney, Agent, or Firm*—Robert M. Schwartz

[57] ABSTRACT

An improved tongue cleaner includes a U-shaped scraper portion and handle portions integrally formed that extend from respective ends of the U-shaped scraper portion. The U-shaped scraper portion has a flange projected perpendicularly from an inner face of the scraper portion and extending therealong to define a corner space on each of two opposed sides of the flange and the inner face for containing matter scraped from the tongue or a user.

5 Claims, 6 Drawing Sheets

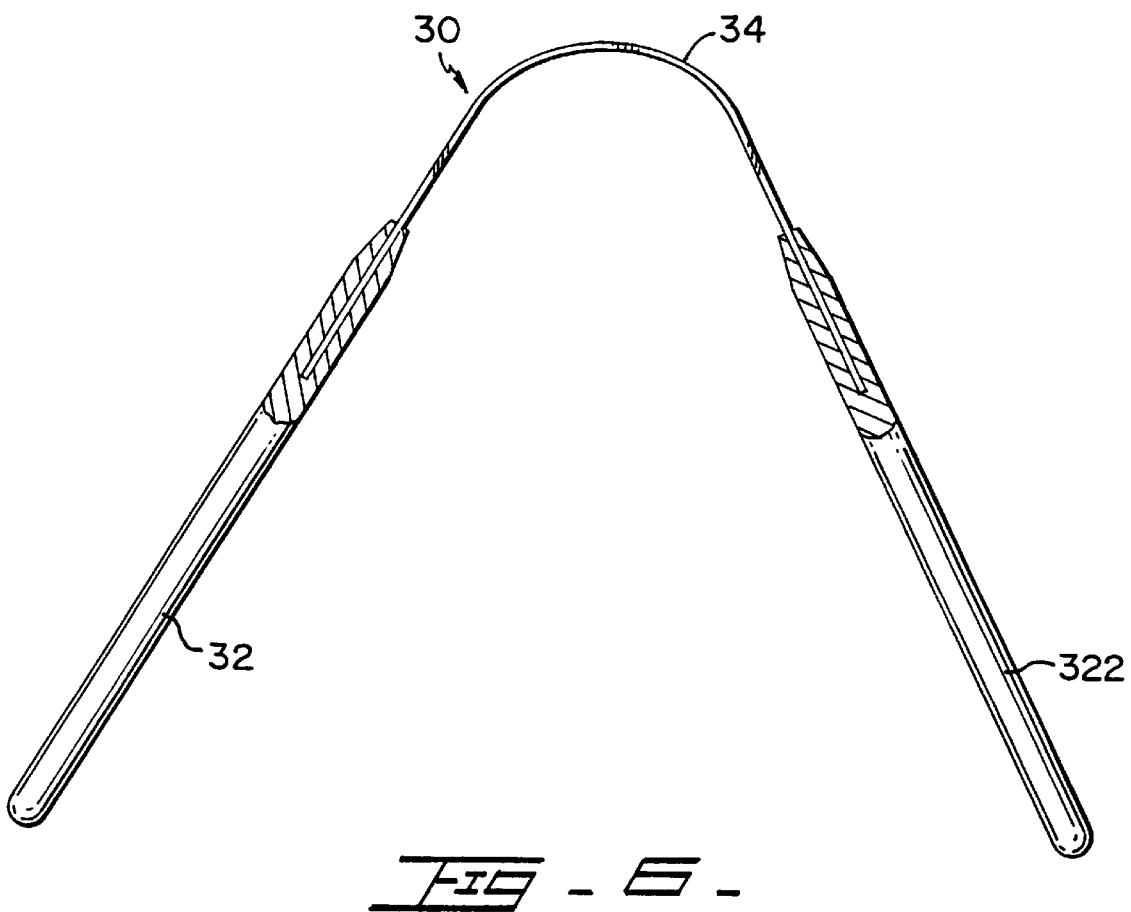

TONGUE CLEANER

CROSS REFERENCES TO RELATED APPLICATIONS

This patent claims the priority date of Taiwan Patent filed on Feb. 5, 1998, by Chung-Yi Lin. The basis for priority in this case is reciprocal legislation in Taiwan.

1. Field of the Invention

The present invention relates to a tongue cleaner and, more particularly, to a tongue cleaner of simple structure which has a corner space for accumulating undesired matter scraped from a tongue of a user.

2. Background of the Invention

A conventional tongue cleaner 30 typically includes a U-shaped scraper plate 34 securely disposed between a pair of handles 32 and 322, as shown on FIGS. 5 and 6. Unpleasant odorous matter may be removed from a person's tongue by that person or another grasping the handles 32, 322 in one hand and placing the scraper plate 34 on his/her mouth to scrape it along an upper surface of his/her tongue. However, construction of the cleaner 30 of such type necessitates complex processes, since the U-shaped plate 34 of the handles 32 and 322 are manufactured separately, and assembled in the configuration shown in FIG. 6 during a subsequent step of welding or any other suitable manner.

An additional problem coming with the conventional cleaner 30 lies in that matter scraped from the tongue of a user will accumulate on an inner face of the scraper plate 34, and moves upward, unobstructed, along the inner face until it reaches an upper edge of the inner face. Eventually the matter may fall into the user's mouth and even be swallowed by mistake.

An additional problem with the conventional cleaner 30 is that the scraper plate must be made out of metal because materials such as plastic break and fold, rather then bend and curve when the two handles are compressed. By having to use metal rather than plastic, the cost of manufacturing are driven up.

SUMMARY OF THE INVENTION

The object of the present invention is to provide a tongue cleaner which can be easily manufactured at a low cost.

Another object of the present invention is to provide a tongue cleaner which has a corner space for containing matter scraped from the tongue of a user to prevent the matter from falling off and back into the mouth.

Another object of the present invention is to provide a tongue cleaner having a reinforced U-shaped scraper portion. A flange added to the inside of the U-shaped scraper portion reinforces the scraper portion.

Another object of the invention is to provide a tongue cleaner having a U-shaped scraper portion whose structure and design allows the use of non-traditional material such as plastic. A flange added to the inner face of the U-shaped scraper portion reinforces the U-shaped scraper portion and allows materials such as plastic to be used to manufacture a U-shaped scraper portion that can bend without fear that the U-shaped scraper portion would bend or crack.

BRIEF DESCRIPTION OF THE DRAWINGS

FIG. 6 is a schematically cross-sectional front view of the tongue cleaner shown in FIG. 5.

DETAILED DESCRIPTION OF PREFERRED EMBODIMENT

Figure 1:
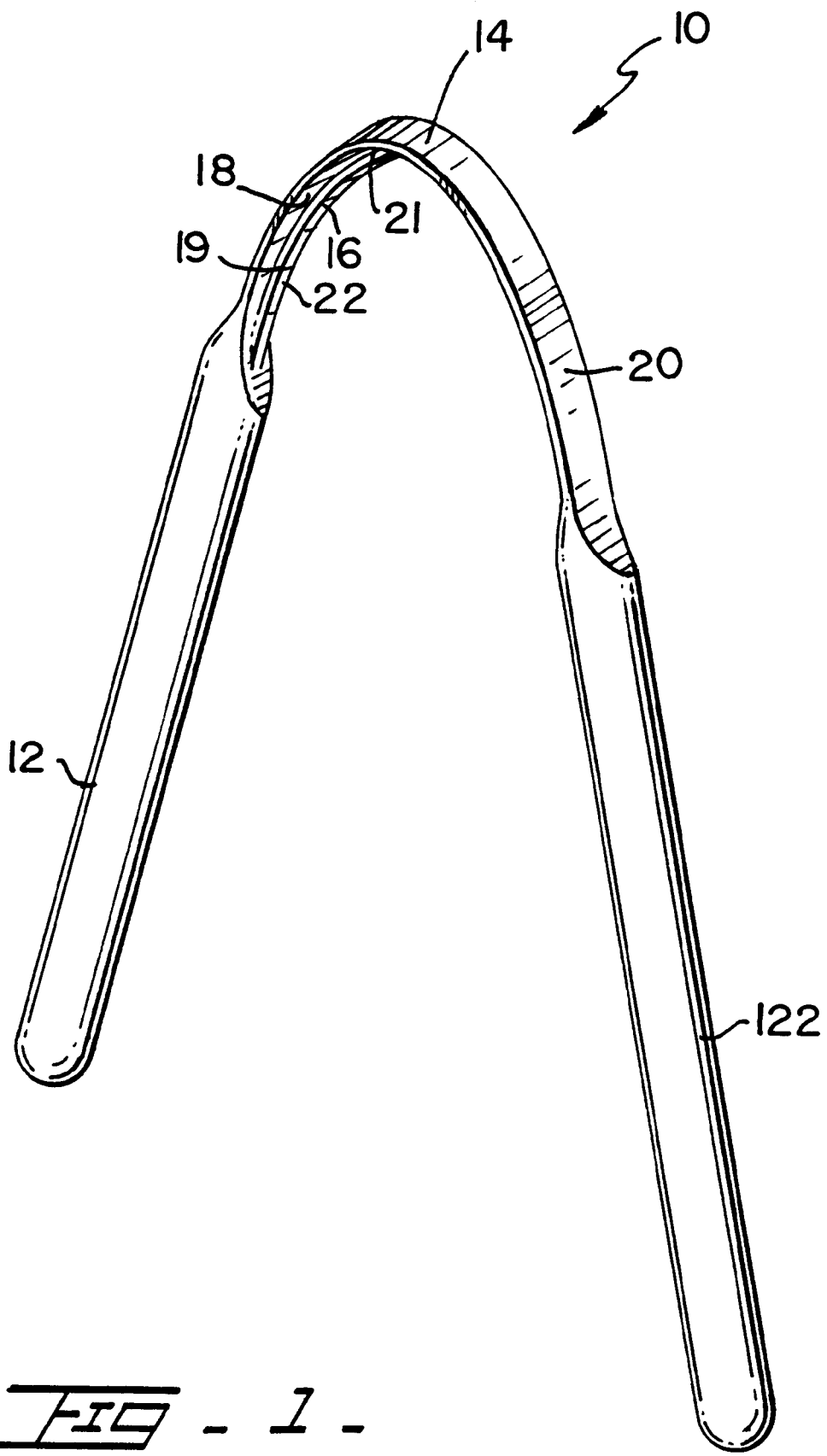
FIG. 1 is a perspective view of a tongue cleaner in accordance with the present invention.
Figure 2:
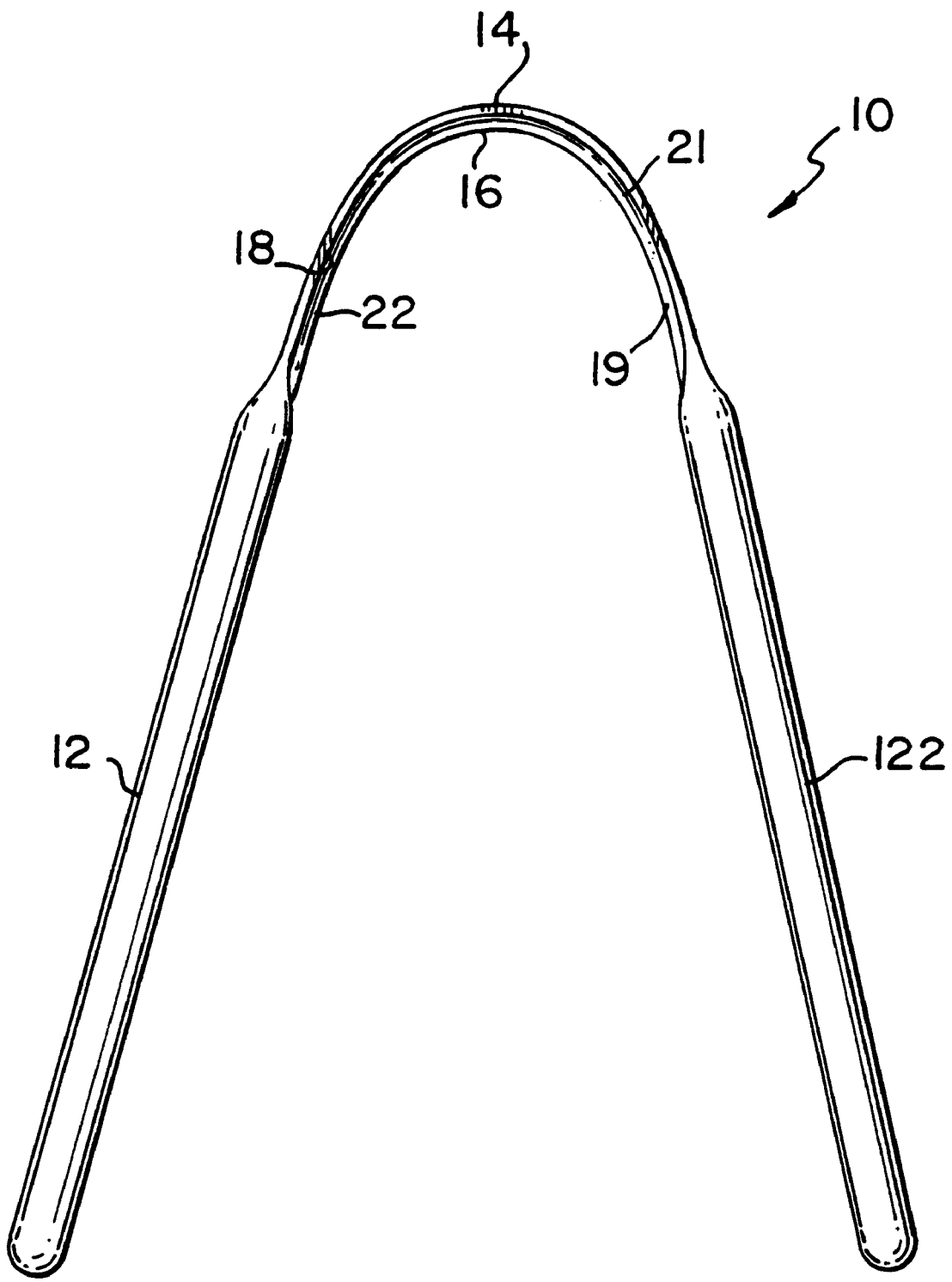
FIG. 2 is a front view of the tongue cleaner shown in FIG. 1.

Referring to FIGS. 1 and 2, the preferred embodiment of a tongue cleaner 10 in accordance with the present invention includes a substantially U-shaped scraper portion 14 integrally formed with handle portions 12, 122 extending from respective ends of the scraper portion 14. In this configuration, a flexible deformation of the U-shaped scraper portion 14 may be achieved by urging the handle portions 12, 122 toward each other.

Figure 3:
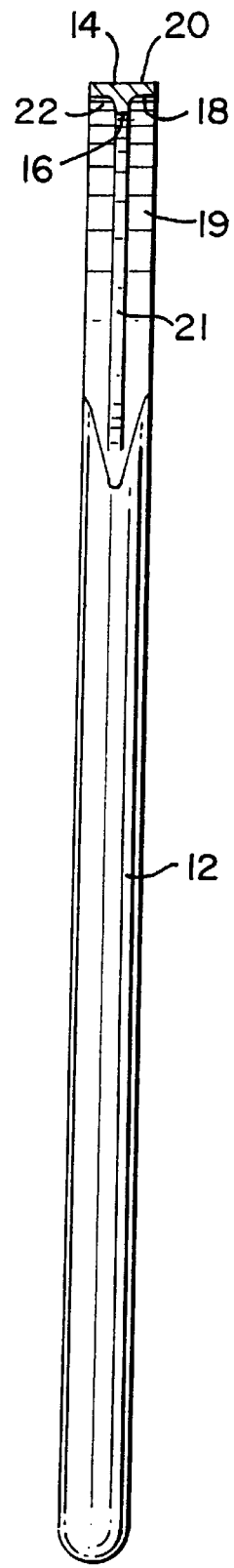
FIG. 3 is a schematic, cross-sectional side view of the tongue cleaner shown in FIGS. 1 and 2.

Referring to FIG. 3, a flange 16 is projected perpendicularly from an inner face 19 of the scraper portion 14 wherein the inner face 19 is the surface on the concave side of U-shaped scraper portion 14. The flange 16 extends along the scraper portion 14 from handle portion 12 to handle portion 122 to define two corner spaces 18 and 22, wherein each corner space is defined by one of the two opposed sides of the flange 16 and the inner face of the scraper portion 14. Corner space 18 catches matter scraped from the tongue of a user. Flange 16 being formed of sufficient depth to contain the particular matter removed from the tongue. Outer surface 20 of scraper portion 14 comprises the convex surface U-shape scraper portion 14.

Preferably, flange 16 extends along a longitudinal center line 21 wherein the longitudinal center line 21 is defined as the line running from handle portion 12 to handle portion 122 along the middle of inner face 19.

Figure 4:
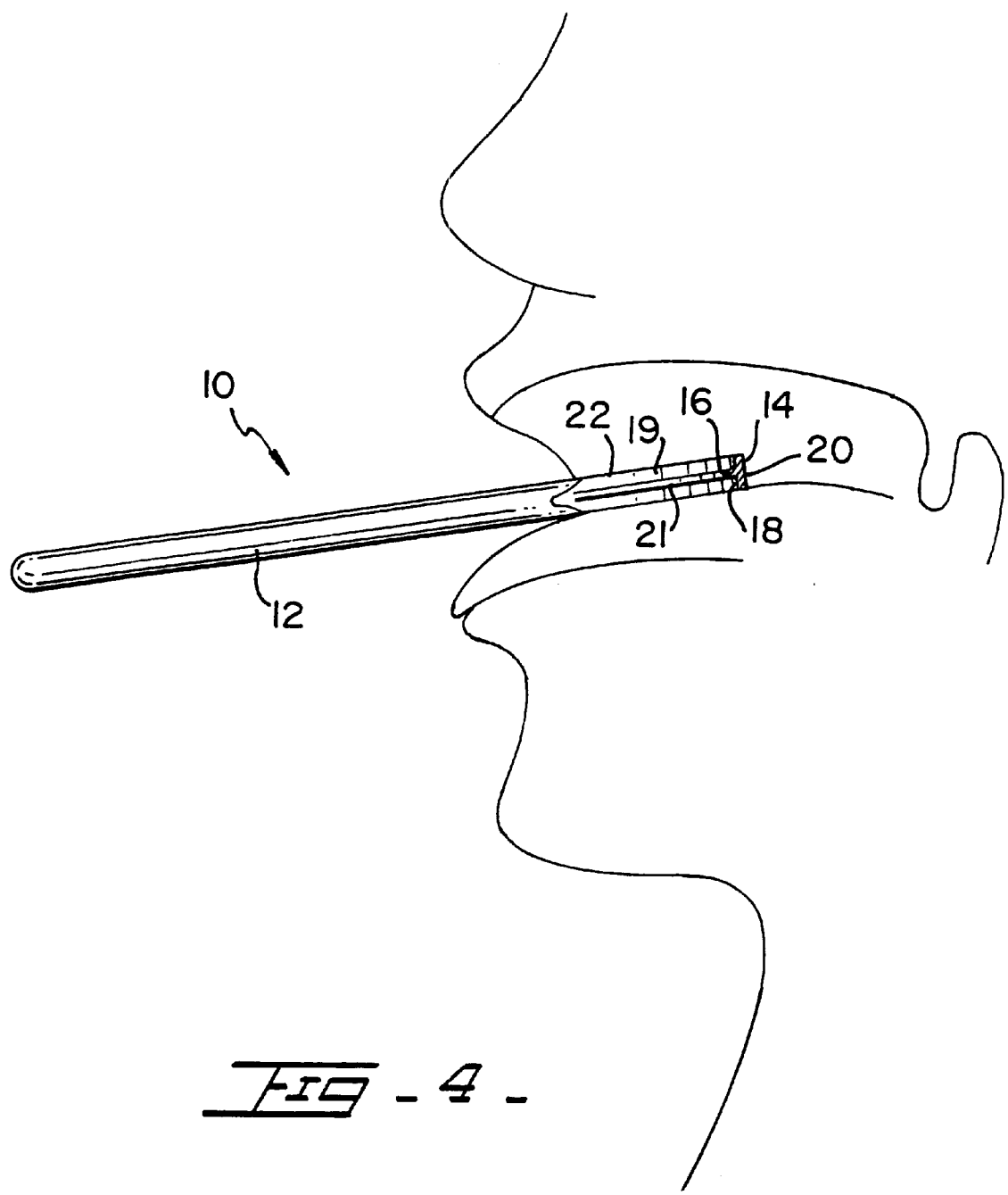
FIG. 4 is a schematic view of the tongue cleaner of the present invention in operation.
Figure 5:
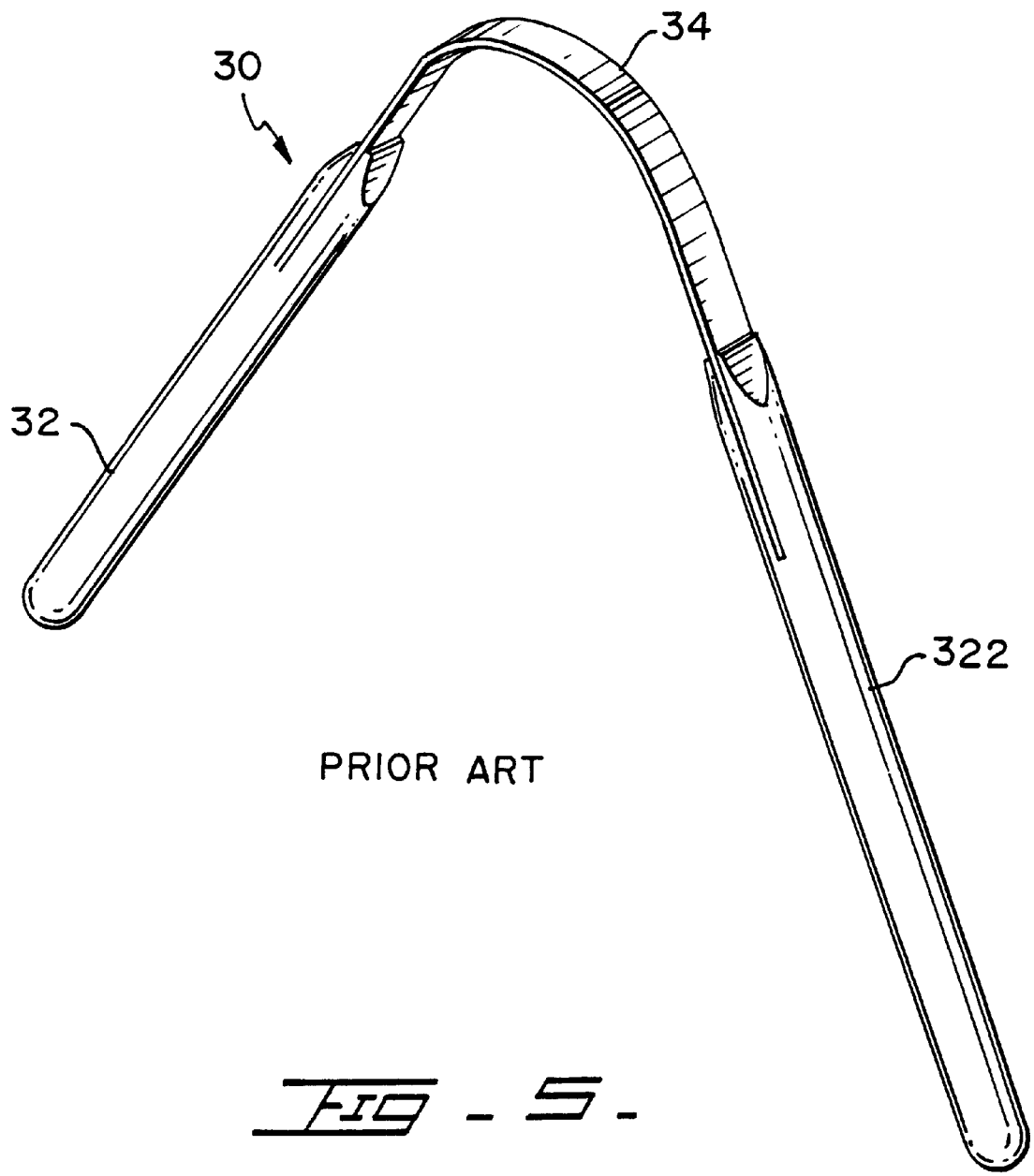
FIG. 5 is a perspective view of a conventional tongue cleaner.

Referring to FIGS. 1 and 4, in operation, the cleaner 10 may be held by using a single hand to grasp both the handle portions 12 and 122. The user puts the scraper portion 14 into his mouth and against his tongue and pulls in a direction from the rear of the mouth towards the front so that the matter on the tongue can be removed therefrom to clean the tongue and remove these materials that cause halitosis.

Due to the direction in which the cleaner 10 is pulled, the matter may be accumulated and adhered to in the inner face of the scraper portion 14 and, particularly, contained within one of the corner spaces 18 and 22. Furthermore, flange 16 stops the excessive movement of the matter, preventing it from running beyond and away off an edge of the inner face which is opposite to the edge in contact to the user tongue. Therefore, the scraped matter will not remain in the mouth and so not be swallowed by the user.

Another advantage of the tongue cleaner 10 of the present invention is derived from the fact that the handle portions 12 and 122 are integrally formed with the scraper portion 14. This simplifies the structure of the cleaner 10 and offers a possibility in fabrication of the cleaner 10 at a relatively low cost.

The preferred material from which the tongue cleaner 10 should be constructed is plastic. Flange 16 when mounted on inner face 19 of U-shaped scraper 14 acts like an I-beam to support U-shaped scraper 14 to allow it to bend in an arc without folding or cracking.

What is claimed is:

1. An improved tongue cleaner, comprising:

a substantially U-shaped flexible scraper portion having an outer face and an inner face, handle portions integrally formed with and extending from respective ends of said U-shaped scraper portion;

said scraper portion having a flange projected perpendicularly from said inner face and extending along said U-shaped scraper portion to define a corner space on each of two opposed sides of said flange and wherein said flange is flexible and projects from said inner face along a longitudinal center line of said scraper portion.

2. An improved tongue cleaner as in claim 1, said outer face and said inner face having common top and bottom edges, wherein said top edge or said bottom edge contacts the tongue to perform a scraping action.

3. An improved tongue cleaner as in claim 1, wherein said corner spaces are substantially symetrical.

4. An improved tongue cleaner as in claim 1, where said flange strengthens said U-shaped scraper.

5. An improved tongue cleaner as in claim 2, wherein said flange is constructed and arranged to contain scraped matter within a said corner space.

\* \* \* \* \*